United States Patent [19]
Fujita et al.

[11] Patent Number: 6,124,219
[45] Date of Patent: Sep. 26, 2000

[54] FUNCTIONAL MATERIAL CONTAINING VOLATILE AGENT

[75] Inventors: Masao Fujita; Koichi Taniguchi; Isao Tomoyasu; Yoshinori Nakano, all of Fukui, Japan

[73] Assignee: Rengo Co., Ltd., Osaka, Japan

[21] Appl. No.: 09/139,109

[22] Filed: Aug. 25, 1998

[30] Foreign Application Priority Data

Aug. 29, 1997 [JP] Japan ................................ 9-234789
Oct. 2, 1997 [JP] Japan ................................ 9-270028
May 18, 1998 [JP] Japan ............................... 10-135469

[51] Int. Cl.$^7$ .................................. B32B 3/26; B32B 5/14
[52] U.S. Cl. .......................... 442/159; 428/199; 428/207; 428/306.6; 428/308.8
[58] Field of Search .................... 428/199, 207, 428/306.6, 308.8; 442/159

[56] References Cited

U.S. PATENT DOCUMENTS 4,624,881  11/1986  Shini ........................................ 428/207
5,389,426  2/1995  Arens et al. ............................. 428/195

*Primary Examiner*—Blaine Copenheaver
*Attorney, Agent, or Firm*—Wenderoth, Lind, & Ponack, L.L.P.

[57] ABSTRACT

A functional material which fades in color with the volatilization of volatile agents such as fragrant agents, deodorant agents, antibacterial agents, etc. so that a user can visually check the end of the effect of such agents. A volatile agent and an oil-soluble dye having a dissolving proportion of 0.0001–1% are carried on a porous carrier undyeable with, i.e. low in affinity for the oil-soluble dye. The content of the oil-soluble dye is 0.1–100 μg per square centimeter of the effective surface area of the porous carrier.

19 Claims, 1 Drawing Sheet

FUNCTIONAL MATERIAL CONTAINING VOLATILE AGENT

BACKGROUND OF THE INVENTION

This invention relates to a functional material using volatile agents such as fragrant agents, deodorant agents, antibacterial agents, antifungal agents and/or mothproofing agents, and containing a dye that permits visual checking of the end of volatilization of the volatile agent.

There is known a material containing a volatile agent such as a fragrant agent and a volatile dye so that the residual amount of the agent and thus its effects are visually checkable based on the degree of fading of the color.

But in such a material, the volatile agent and the dye do not necessarily volatilize at the same rate. Thus, if the dye volatilizes completely before does the volatile agent, a user may judge that the volatile agent has also gone completely and discard the material in spite of the fact that there still remains a considerable amount of volatile agent. Conversely, the volatile agent may volatilize completely before does the dye. In such a case, a user will keep using the material in spite of the fact that it has no effects any more.

There is also known a material containing a volatile agent and an organic color compound so that the effects of the agent are visually checkable based on the change in color of the compound resulting from its chemical change with the volatilization of the volatile agent. In this case, although there is no problem of time difference between the expiration of effects of the agent and the color change, the combination of a volatile agent and an organic color compound poses a big problem. In other words, the kind of volatile agents usable in combination with a particular organic color compound is very limited. Also, even if the combination is possible, most organic color compounds tend to deepen in color with volatilization of the agent. Deep color tends to give a wrong impression to a user that the material is brand-new and contains an ample amount of volatile agent even when actually the agent has run out.

An object of the present invention is to provide a functional material that makes it possible to visually check the end of volatilization of a volatile agent from the degree of fading of the color, and to use practically any kind of volatile agents in which an oil-soluble dye is dissolvable.

SUMMARY OF THE INVENTION

According to this invention, there is provided a functional material comprising a volatile agent, an oil-soluble dye having a dissolving proportion of 0.0001–1%, and a porous carrier undyeable with the oil-soluble dye and having pores, the volatile agent and the oil-soluble dye being retained in the pores, whereby making it possible to visually check the end of volatilization of the volatile agent, the content of the oil-soluble dye being 0.1–100 $\mu$g per square centimeter of the effective surface area of the porous carrier.

The "dissolving proportion" as used in this invention is given by the following equation.

$$\text{Dissolving Proportion (\%)} = \frac{\text{Max Weight (g) of oil-soluble dye dissolved in volatile agent}}{\text{Weight (g) of volatile agent}} \times 100$$

The "effective surface area" of the porous carrier as used in this invention is twice the maximum shadow area of the carrier created by light from a light source at an infinitely far spot (such as the sun). For example, a sphere with a radius r has an effective area of $2\times\pi r^2$. A sheet or mat having a length a, a width b and a thickness c (a and b being far greater than c) has an effective surface area of 2×ab.

If a volatile agent is still present in the material, the dye is dissolved in the volatile agent, thus coloring the agent. In this case, since the agent present uniformly in the pores of the porous carrier is colored, the entire functional material looks colored to the human eye. During the period while the volatile agent is volatilizing, too, the volatile agent in which the dye is dissolved still exists in the pores of the porous carrier, so that the entire functional material still looks colored (see schematic view of FIG. 1).

When the volatile agent has volatilized nearly completely, the dye dissolved in the volatile agent will separate on the surface of the carrier instead of dyeing in the carrier because the carrier has no affinity for the dye. If the amount of dye is small, the surface area of the solid dye that has separated is small compared with the surface area of the carrier. Thus, the entire functional material manifests the color of the carrier itself. For example, if an agent dyed blue is carried on a white carrier, the white color of the carrier will appear when the volatile agent has volatilized nearly completely. Thus the functional material turns from blue to white as the volatile agent volatilizes. Thus, a user can visually check the fact that the agent has gone by the color of the functional material. The change in color of the functional material is not due to the change in color of the dye itself but due to the separation of the dye and the resulting reduction in the dyed area with respect to the entire surface of the carrier. In this state, to the human eye, only the color of the carrier is conspicuous while the color of the dye is scarcely perceptible (see schematic view of FIG. 2).

Such change in color notifies a user the end of volatilization of the volatile agent.

In FIGS. 1 and 2, numeral 1 indicates the carrier, 2 the dissolved dye, and 2' the dye that has separated.

If the volatile agent works as an effective component such as a fragrant, an anti-bacterial agent and a deodorant, the material of the present invention functions to indicate the expiration of agent effect by change in color. If not, the material serves as an indicator by controlling the period required for the volatilization of the volatile agent.

The change in color of the functional material is closely related to the dissolving proportion of the oil-soluble dye, and its amount per unit effective surface area of the porous carrier.

If the dissolving proportion is less than 0.0001%, the agent will not be colored when impregnated with the dye. If it exceeds 1%, the dye will separate while spreading over the carrier like a film. Thus even when the agent has valatilized, the color of the material will not vanish.

If the content of the oil-soluble dye is less than 0.1 $\mu$g per square centimeter of the effective surface area of the porous carrier, it would be impossible to color the entire carrier by impregnation of the agent. If over 100 $\mu$g per square centimeter, the entire carrier surface would be covered by the separated dye when the agent has volatilized. Thus, the color of the material will not vanish.

The volatile agent used in this invention may be any substance that is volatile and liquid at normal temperature. Such volatile agents include mothproofing agents/repellents such as pyrethroid and peppermint oil; perfumes such as pinene, limonene, camphene, terpinolene, linalool, geraniol, citronellol, citral, benzaldehyde, carvone, menthone, coumarin, anisole, thymol, eugenol, anethole, cinnamic acid, phenylacetic acid, hydrocinnamic acid, ethyl acetate, geranyl acetate, isoamyl propionate, rose oxide, oxide ketone, cineole, indole, skatole, methyl quinoline, musk, civet, castreum, ambergris, lemon oil, rose oil, sandalwood oil, lavender oil and jasmine oil; antibacterial/antifungal agents such as allyl isothiocyanate, octyl aldehyde and bromocinnamic aldehyde; essential oils/deodorant agents such as hiba oil, hinoki oil, bamboo extract, mugwort extract, tung oil, fragrant olive extract, tsubaki oil, eucalyptus oil, horse-radish extract, mustard oil and getto oil; and alcohols such as methanol, ethanol and propylene glycol.

Oil-soluble dyes usable in the present invention include disperse dyes such as C.I.Disp.Red54, C.I.Disp.Red60, C.I.Disp.Red73, C.I.Disp.Red92, C.I.Disp. Yellow 51, C.I.Disp. Yellow 54, C.I.Disp. Yellow 64, C.I.Disp. Yellow 79, C.I.Disp.Blue56, C.I.Disp.Blue79, C.I.Disp.Blue81, and C.I.Disp.Blue 139, solvent dyes such as C.I.Solvent Red23, C.I.Solvent Red24, C.I.Solvent Red26, C.I.Solvent Yellow2, C.I.Solvent Yellow7, C.I.Solvent Yellow14, C.I.Solvent Blue37, and C.I.Solvent Blue38, and vat dyes.

As the carrier, a material that is not dyed by the above-mentioned dye should be selected. Such materials include cellulosic porous materials such as paper, woven fabric, nonwoven fabric, wood flour, pulp sheet, pulp mat, cellulosic sponge, and cellulosic particles; hydrophilic porous polymers in the form of woven fabric, nonwoven fabric, sponge or porous particles of such material as starch, polyvinyl alcohol, alginate salt, casein, collagen, polyamide and polyacrylic acid; hydrophobic porous polymers impregnated with hydrophilic material in the form of woven fabric, nonwoven fabric, sponge or porous particles of polyurethane impregnated with hydrophilic material, polyethylene impregnated with hydrophilic material, or polypropylene impregnated with hydrophilic material; porous cellulosic derivatives in the form of woven fabric, nonwoven fabric, sponge or porous particles of cellulose acetate, nitrocellulose, ethyl cellulose or carboxymethyl cellulose; and inorganic porous materials in the form of porous particles of silicate salt, silica gel, zeolite or alumina.

If a carrier dyeable with a dye is used, the carrier will be dyed when the volatile agent has volatilized. Thus, such a carrier is not usable because the functional material will not change its color.

The volatile agent may be impregnated after embedding the dye in the pores of the porous carrier with an embedding material such as wax. The embedding material may be a mineral wax such as ozocerite, a petroleum wax such as paraffin wax and microcrystalline wax, a natural wax such as fatty acid, stearic acid, carnauba wax and rice wax, or a substance which is solid at normal temperature such as stearyl alcohol, benzoic acid and BHT. If the carrier is a white one, a white solid material should be used.

In order to fix the dye in the pores of the porous carrier with the embedding material, the wax may be melted and kneaded with a dye, and the kneaded liquid be embedded in the pores of the porous carrier.

Otherwise, a molten embedding material may be kneaded with an oil-soluble dye and a volatile agent beforehand and be embedded in the pores of the porous carrier.

The functional material in which a dye is embedded in the pores of a porous carrier is more preferable because it is possible to prevent the dye from moving toward the surface of the carrier with volatilization of the volatile agent and separating as big crystals at the surface of the carrier.

Other features and objects of the present invention will become apparent from the following description made with reference to the accompanying drawings, in which:

DETAILED DESCRIPTION OF THE PREFERRED EMBODIMENT

Figure 1:
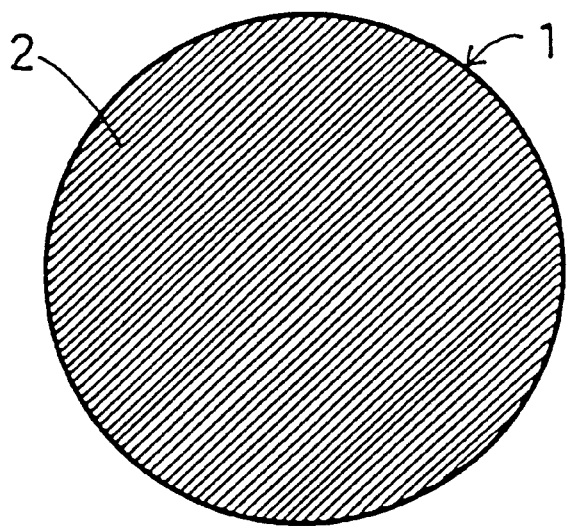
FIG. 1 is a schematic view showing the state in which a dye is dissolved in a volatile agent in a liquid form, covering the pores of a carrier.
Figure 2:
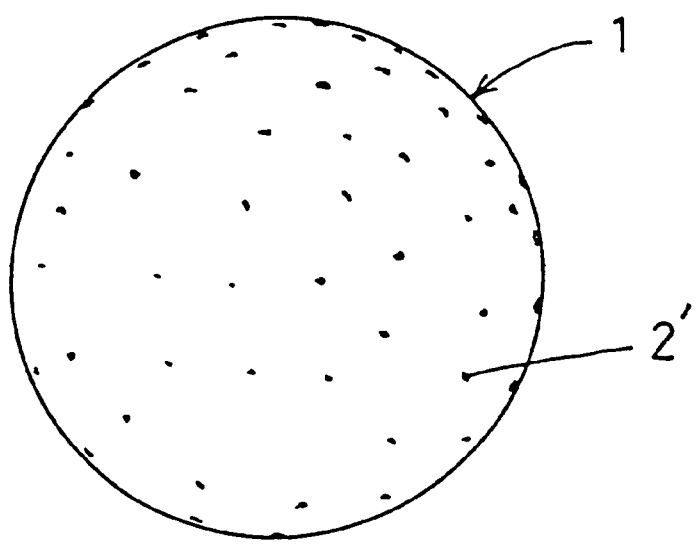
FIG. 2 is another schematic view showing the state in which the volatile agent has volatilized and the dye locally flocculates and separates in the pores of the carrier, thus exposing the surface of the carrier.

The following experiments were conducted as Examples of this invention and Comparative Examples. The results are shown in Table 1.

EXAMPLE 1

A solution including 300 g of allyl isothiocyanate (hereinafter referred to as "AIT") as a lipophilic volatile agent in which was dissolved 30 mg of Disp.Blue 79 as a disperse dye was prepared. 3 g of this solution (containing 300 $\mu$g of disperse dye) was impregnated into 4 g of cellulosic beads (VISCOPEARL made by RENGO; effective surface area: 300 $cm^2$). The thus impregnated beads were left at room temperature to let AIT volatilize completely. The color change was judged by visually checking the color of the beads when the solution has been prepared and when AIT has volatilized completely.

EXAMPLE 2

This Example is the same as Example 1 except that 6 mg of dye was dissolved in AIT (dye content in 3 g of solution: 60 $\mu$g).

EXAMPLE 3

This Example is the same as Example 1 except that 600 mg of dye was dissolved in AIT (dye content in 3 g of solution: 6 mg).

EXAMPLE 4

This Example is the same as Example 1 except that the carrier was 16 g of cellulosic mat (effective surface area: 300 $cm^2$) instead of cellulosic beads.

EXAMPLE 5

This Example is the same as Example 1 except that limonene was used as the volatile agent instead of AIT.

EXAMPLE 6

This Example is the same as Example 1 except that 2 g of calcium silicate (effective surface area: 300 $cm^2$) was used as the carrier.

EXAMPLE 7

This Example is the same as Example 1 except that the dye used was Solvent Red 1 which was a Solvent dye.

EXAMPLE 8

30 mg of Disp. Blue 79 and 20 g of molten paraffin wax were mixed together, and 0.2 g of the mixture (dye content: 300 $\mu$g) was dipped in 4 g of cellulosic beads (effective surface area: 300 $cm^2$) and let to cool. The thus obtained composite beads was then impregnated with 3 g of AIT. Otherwise, this Example is the same as Example 1.

EXAMPLE 9

0.3 mg of Disp. Blue 79 as a disperse dye and 5 g of paraffin wax were mixed with 3 g of AIT and kneaded while heating. The liquid thus obtained was impregnated into 4 g of cellulosic beads. Otherwise, this Example is the same as Example 1.

EXAMPLE 10

This Example is the same as Example 9 except that the volatile agent used was limonene.

EXAMPLE 11

This Example is the same as Example 9 except that stearic acid was used as an embedding material instead of paraffin wax.

EXAMPLE 12

This Example is the same as Example 9 except that the carrier used was calcium silicate.

EXAMPLE 13

This Example is the same as Example 9 except that the dye used was Solvent Red 1, a Solvent dye.

COMPARATIVE EXAMPLE 1

This Example is the same as Example 1 except that 1.5 mg of dye was dissolved in AIT. (15 μg of dye in 3 g of solution).

COMPARATIVE EXAMPLE 2

This Example is the same as Example 3 except that 0.4 g of cellulosic beads (effective surface area: 30 cm$^2$) was used.

COMPARATIVE EXAMPLE 3

This Example is the same as Example 1 except that 30 mg of a water-soluble dye Acid Blue 112 was dispersed in 300 g of AIT.

COMPARATIVE EXAMPLE 4

This Example is the same as Example 1 except that a solvent dye Solvent Blue 35 was used as the dye.

COMPARATIVE EXAMPLE 5

This Example is the same as Example 9 except that the volatile agent used was ethanol in which an oil-soluble dye is undissolvable.

COMPARATIVE EXAMPLE 6

This Example is the same as Example 9 except that the carrier used was foamed polyurethane which is dyeable with an oil-soluble dye.

According to this invention, the color or tone changes, specifically fades, in direct relation with degree of volatilization of the volatile agent. That is, it is possible to visually confirm the end of volatilization of the volatile agent with high reliability. It is possible to use any volatile agent in which an oil-soluble dye is dissolved. The material in which the volatile agent is embedded in the pores of the porous carrier by an embedding material is high in the effect of control release of the agent.

TABLE 1

| | Carrier | Dye | Agent | Embedding material | A | B | Tone |
|---|---|---|---|---|---|---|---|
| 1 | Cellulosic bead | Disp.B.79 | AIT | — | 1 | 0.2 | blue → white |
| 2 | ↑ | ↑ | ↑ | — | 0.2 | ↑ | ↑ |
| 3 | ↑ | ↑ | ↑ | — | 20 | ↑ | ↑ |
| 4 | Cellulosic mat | ↑ | ↑ | — | 1 | ↑ | ↑ |
| 5 | Cellulosic bead | ↑ | limonene | — | ↑ | 0.03 | ↑ |
| 6 | Calcium silicate | ↑ | AIT | — | ↑ | 0.2 | ↑ |
| 7 | Cellulosic bead | Solvent R.1 | ↑ | — | ↑ | 0.4 | red → white |
| 8 | Cellulosic bead | Disp.B.79 | ↑ | paraffine wax embedded and agent impregnated | ↑ | 0.2 | blue → white |
| 9 | ↑ | ↑ | ↑ | paraffine wax mixed with agent and embedded | ↑ | ↑ | ↑ |
| 10 | ↑ | ↑ | limonene | ↑ | ↑ | 0.03 | ↑ |
| 11 | ↑ | ↑ | AIT | stearic acid mixed with agent and embedded | ↑ | 0.2 | ↑ |
| 12 | Calcium silicate | ↑ | ↑ | paraffine wax mixed with agent and embedded | ↑ | ↑ | ↑ |
| 13 | Cellulosic bead | Solvent R.1 | ↑ | ↑ | ↑ | 0.4 | red → white |

TABLE 1-continued

| | Carrier | Dye | Agent | Embedding material | A | B | Tone |
|---|---|---|---|---|---|---|---|
| C1 | Cellulosic bead | Disp.B.79 | ↑ | — | 0.05 | ↑ | white → white |
| C2 | ↑ | ↑ | ↑ | — | 200 | ↑ | blue → blue |
| C3 | ↑ | Acid B.112 | ↑ | — | 1 | 0.00005 | white → white |
| C4 | ↑ | Solvent B.35 | ↑ | — | ↑ | 1.2 | blue → blue |
| C5 | ↑ | Disp.B.79 | ethanol | paraffine wax mixed with agent and embedded | ↑ | 0 | white → white |
| C6 | foamed polyurethane | ↑ | AIT | ↑ | ↑ | 0.2 | blue → blue |

A Amount of dye per effective surface area of carrier (in $\mu g/cm^2$)
B Dissolving proportion of dye (in %)

What is claimed is:

1. A functional material comprising a volatile agent, an oil-soluble dye having a dissolving proportion of 0.0001–1%, and a porous carrier undyeable with said oil-soluble dye and having pores, said volatile agent and said oil-soluble dye being retained in said pores, thereby making it possible to visually check the end of volatilization of said volatile agent, the content of said oil-soluble dye being 0.1–100 $\mu$g per square centimeter of the effective surface area of said porous carrier.

2. A functional material as claimed in claim 1 wherein said porous carrier is a cellulosic porous material of cellulosic bead, cellulosic sponge or paper, or a woven or nonwoven fabric made of hydrophilic fiber, or a hydrophilic porous material.

3. A functional material as claimed in claim 2 wherein said oil-soluble dye is mixed and kneaded with an embedding material which is a mineral wax, a petroleum wax, or a natural wax, the kneaded mixture is embedded in said pores of said porous carrier, and said porous carrier is impregnated with said volatile agent.

4. A functional material as claimed in claim 3 wherein said mineral wax is ozocerite.

5. A functional material as claimed in claim 3 wherein said petroleum wax is paraffin wax or microcrystalline wax.

6. A functional material as claimed in claim 3 wherein said natural wax is a fatty acid wax, carnauba wax or rice wax.

7. A functional material as claimed in claim 2 wherein said oil-soluble dye and said volatile agent are mixed and kneaded with an embedding material which is a mineral wax, a petroleum wax, or a natural wax, the mixture is embedded in said pores of said porous carrier.

8. A functional material as claimed in claim 7 wherein said mineral wax is ozocerite.

9. A functional material as claimed in claim 7 wherein said petroleum wax is paraffin wax or microcrystalline wax.

10. A functional material as claimed in claim 7 wherein said natural wax is fatty acid wax, carnauba wax or rice wax.

11. A functional material as claimed in claim 2 wherein said hydrophilic porous material is calcium silicate, alumina, silica gel or zeolite.

12. A functional material as claimed in claim 1 wherein said oil-soluble dye is mixed and kneaded with an embedding material which is a mineral wax, a petroleum wax, or a natural wax, the kneaded mixture is embedded in said pores of said porous carrier, and said porous carrier is impregnated with said volatile agent.

13. A functional material as claimed in claim 12 wherein said mineral wax is ozocerite.

14. A functional material as claimed in claim 12 wherein said petroleum wax is paraffin wax or microcrystalline wax.

15. A functional material as claimed in claim 12 wherein said natural wax is a fatty acid wax, carnauba wax or rice wax.

16. A functional material as claimed in claim 1 wherein said oil-soluble dye and said volatile agent are mixed and kneaded with an embedding material which is a mineral wax, a petroleum wax such, or a natural wax, the mixture is embedded in said pores of said porous carrier.

17. A functional material as claimed in claim 16 wherein said mineral wax is ozocerite.

18. A functional material as claimed in claim 16 wherein said petroleum wax is paraffin wax or microcrystalline wax.

19. A functional material as claimed in claim 16 wherein said natural wax is a fatty acid wax, carnauba wax or rice wax.

* * * * *